United States Patent
Rozencweig et al.

(10) Patent No.: US 8,026,267 B2
(45) Date of Patent: Sep. 27, 2011

(54) NON-PEGYLATED LIPOSOMAL DOXORUBICIN TRIPLE COMBINATION THERAPY

(75) Inventors: Marcel Rozencweig, Princeton, NJ (US); Ronald H. Goldfarb, Guilford, CT (US); Salvatore Forenza, Exton, PA (US)

(73) Assignee: Sopherion Therapeutics, LLC, East Brunswick, NJ (US)

( * ) Notice: Subject to any disclaimer, the term of this patent is extended or adjusted under 35 U.S.C. 154(b) by 0 days.

(21) Appl. No.: 12/880,037

(22) Filed: Sep. 10, 2010

(65) Prior Publication Data

US 2010/0323004 A1    Dec. 23, 2010

Related U.S. Application Data

(63) Continuation of application No. 12/756,924, filed on Apr. 8, 2010.

(60) Provisional application No. 61/294,712, filed on Jan. 13, 2010, provisional application No. 61/167,747, filed on Apr. 8, 2009.

(51) Int. Cl.
*A61K 31/415* (2006.01)
(52) U.S. Cl. .................................................... 514/395
(58) Field of Classification Search .................... 514/395
See application file for complete search history.

(56) References Cited

OTHER PUBLICATIONS

Amadori et al., Phase II study of liposomal doxorubicin (Myocet®), docetaxel, and trastuzumab combination as first line treatment of patients with her-2/new positive locally advanced or metastatic breast cancer. 31st Annual San Antonio Breast Cancer Symposium Dec. 2008. Cancer Res. 2009 vol. 69, No. 2 Supp. S, pp. 247S.
Baselga et al, Results of a phase II study of liposomal doxorubicin (Myocet) in combination with weekly paclitaxel and trastuzumab (Herceptin) in patients with HER2-positive locally advanced or metastatic breast cancer (LA/MBC). EJC Supplements 2004 2(3):132, Abst 262.
Batist et al., Improved anti-tumor response rate with decreased cardiotoxicity of non-pegylated liposomal doxorubicin compared with conventional doxorubicin in first line treatment of metastatic breast cancer patients who had received prior adjuvant doxorubicin: results of a retrospective analysis. Anti-Cancer Drugs 2006 17:587-595.
Bianchi et al., Pilot Trial of Trastuzumab Starting with or after the Doxorubicin Component of a Doxorubicin plus Paclitaxel Regimen for Women with HER2-Positive Advanced Breast Cancer. Clin. Cancer Res. 2003 9:5944.
Cortes et al., Nonpegylated Liposomal Doxorubicin (TLC-D99), Paclitaxel, and Trastuzumab in HER2-Overexpressing Breast Cancer: A Multicenter Phase I/II Study. Clin. Cancer Res. 2009 15(1):307.
Cortes et al., Updated results of a phase II study (M77035) of Myocet® combined with weekly Herceptin® and paclitaxel in patients (pts) with HER2-positive locally advanced or metastatic breast cancer (LABC/MBC). 27th Annual San Antonio Breast Cancer Symposium Dec. 2004 Breast Cancer Res. Treat. 2004 88 (Suppl 1):S125, Abst 3041.
Del Barco et al., Non-pegylated liposomal doxorubicin combined wirth gemcitabine as first-line treatment for metastatic or locally advanced breast cancer. Final results of a phase I/II trial. Breast Cancer Research and Treatment, vol. 116, No. 2, Oct. 22, 2008, pp. 351-358.
PCT/US2010/030441 International Search Report and Written Opinion mailed Jul. 2, 2010.
Stavridi et al., Efficacy and toxicituy of nonpegylated liposomal doxorubicin in breast cancer. Expert Review of Anticancer Therapy Dec. 2008 vol. 8, No. 12, pp. 1859-1869.
Theodoulou et al., Cardiac safety and efficacy of TLC D99 (D99) and trastuzumab in patients with advanced breast cancer. European Journal of Cancer vol. 37, Apr. 1, 2001, p. S195 (Absract).
Trigo et al., Cardiac safety and activity of a phase I study of 3-weekly myocet in combination with weekly herceptin and paclitaxel in HER2-positive (HER2+) locally advanced or metastatic breast cancer (LA/MBC). Proc. Am. Soc. Clin. Oncol. 2002 21, Abst 242.
Trigo et al., Liposomal Doxorubicin (Myocet®) in combination with Herceptin® and paclitaxel, is active and well-tolerated in patients with HER2-positive locally advanced or metastatic breast cancer (LA/MBC): A Phase II study. Breast Cancer Res. Treat. 2003 82:S83, Abst 351.
Vanturini et al, A multi-center Phase II study of non-pegylated liposomal doxorubicin (Myocet®) in combination with trastuzumab and docetaxel as first line therapy in metastatic breast cancer. 31st Annual San Antonio Breast Cancer Symposium Dec. 2008. Cancer Res. 2009 vol. 69, No. 2 Supp. S, pp. 249S.

*Primary Examiner* — Brandon Fetterolf
*Assistant Examiner* — Christopher R Stone
(74) *Attorney, Agent, or Firm* — Cooley, LLP

(57) ABSTRACT

The present invention relates to a method for treating metastatic breast cancer in an individual comprising administering to an individual in need thereof a dosing regimen which comprises administering to the individual nonpegylated liposomal doxorubicin, a taxane and a HER2/neu receptor antagonist, wherein the individual previously has been administered an anthracycline.

13 Claims, 1 Drawing Sheet

NON-PEGYLATED LIPOSOMAL DOXORUBICIN TRIPLE COMBINATION THERAPY

RELATED APPLICATIONS

This application is a continuation of U.S. patent application Ser. No. 12/756,924, filed Apr. 8, 2010, which claims priority under 35 U.S.C. §119(e) to U.S. Provisional Application No. 61/294,712, filed Jan. 13, 2010, and to U.S. Provisional Application No. 61/167,747, filed Apr. 8, 2009, the contents of each of which is hereby incorporated by reference herein in its entirety for all purposes.

FIELD OF THE INVENTION

The present invention is in the field of treatment for metastatic breast cancer in an individual who has previously been administered an anthracycline.

BACKGROUND OF THE INVENTION

Breast cancer is one of the most common causes of cancer deaths in women. In the United States, it accounts for 30% of all malignancies that affect women, excluding non-melanoma skin cancer. About one-third of newly diagnosed patients will eventually recur and/or develop metastatic disease.

Approximately 25% of patients with breast cancer have tumors that over-express HER2. Data from large, international trials of adjuvant regimens for primary breast cancer in the pre-trastuzumab era have shown a significant survival benefit with anthracycline-containing regimens compared to non-anthracycline regimens in breast cancer patients who had strongly HER2+ tumors. An anthracycline based regimen is recommended in most cases for women with node positive breast cancer as well as high risk pre-menopausal women with node negative breast cancer.

Doxorubicin is one of the most active and versatile anti-cancer agents. It has an exceptionally broad spectrum of activity and plays a leading role in the curative and palliative therapy of a diverse group of malignancies, most notably breast cancer, lymphoma, soft tissue sarcoma, various pediatric malignancies, multiple myeloma, and advanced bladder cancer. However, doxorubicin is associated with serious and sometimes life threatening side effects. In particular, doxorubicin's use is limited by the potential for patients to suffer irreversible cardiotoxicity. The incidence of clinically significant cardiomyopathy or congestive heart failure rises with increasing lifetime cumulative doses of doxorubicin. For this reason, most clinicians limit a patient's lifetime cumulative dose of doxorubicin to 450 mg/m$^2$ or less. Sub-clinical and occasionally overt cardiotoxicity may also occur at lower cumulative doses of doxorubicin, especially when the drug is given as part of a combination regimen that includes drugs such as cyclophosphamide or paclitaxel, as well as newer biologic therapies, including trastuzumab.

Clinically relevant cardiotoxicity has been a particular issue in combination regimens of doxorubicin and the taxanes, especially paclitaxel, and to a lesser extent docetaxel and albumin-bound paclitaxel (Abraxan®). Three-fold greater cardiac toxicity was seen in women receiving the combination of trastuzumab and an anthracycline (either doxorubicin or epirubicin) and cyclophosphamide (AC), compared with the rates of cardiotoxicity that would have been expected with AC or trastuzumab alone. The same clinical trials also suggested that despite the high rates of cardiac toxicity, the combination of anthracyclines with trastuzumab (and cyclophosphamide) might actually be more efficacious in the metastasized breast cancer (MBC) setting compared to the FDA-approved paclitaxel/trastuzumab regimen. In particular, improved efficacy with AC and trastuzumab compared with paclitaxel/trastuzumab was notable with respect to time to disease progression and overall survival.

Doxorubicin and trastuzumab are known to be cardiotoxic, and their concomitant combined use presents a significant risk of cardiotoxicity. The risk of cardiotoxicity from treatment with doxorubicin and trastuzumab is believed to be enhanced for patients who have received prior treatment with an anthracycline.

Patients with HER2+ breast cancer have been treated with nonpegylated liposomal doxorubicin in combination with paclitaxel and trastuzumab in Phase I and Phase II clinical trials. Patients who received prior administration of any anthracycline were excluded from these earlier trials, due to the anticipated cardiotoxicity from accumulated anthracycline dosing.

Accordingly, it is an object of the present invention to provide a method for treating metastatic breast cancer in an individual who has previously been administered an anthracycline.

SUMMARY OF THE INVENTION

The present invention relates to a method for treating metastatic breast cancer in an individual comprising administering to an individual in need thereof a dosing regimen which comprises administering to the individual nonpegylated liposomal doxorubicin, a taxane and a HER2/neu receptor antagonist, wherein the individual previously has been administered an anthracycline.

The present invention also provides a method for treating metastatic breast cancer in an individual comprising administering to an individual in need thereof a dosing regimen which comprises administering to the individual nonpegylated liposomal doxorubicin, trastuzumab and a chemotherapeutic agent selected from the group consisting of capecitabine, vinorelbine, gemcitabine and carboplatin, wherein said individual previously has been administered an anthracycline.

DETAILED DESCRIPTION OF THE INVENTION

Figure 1:
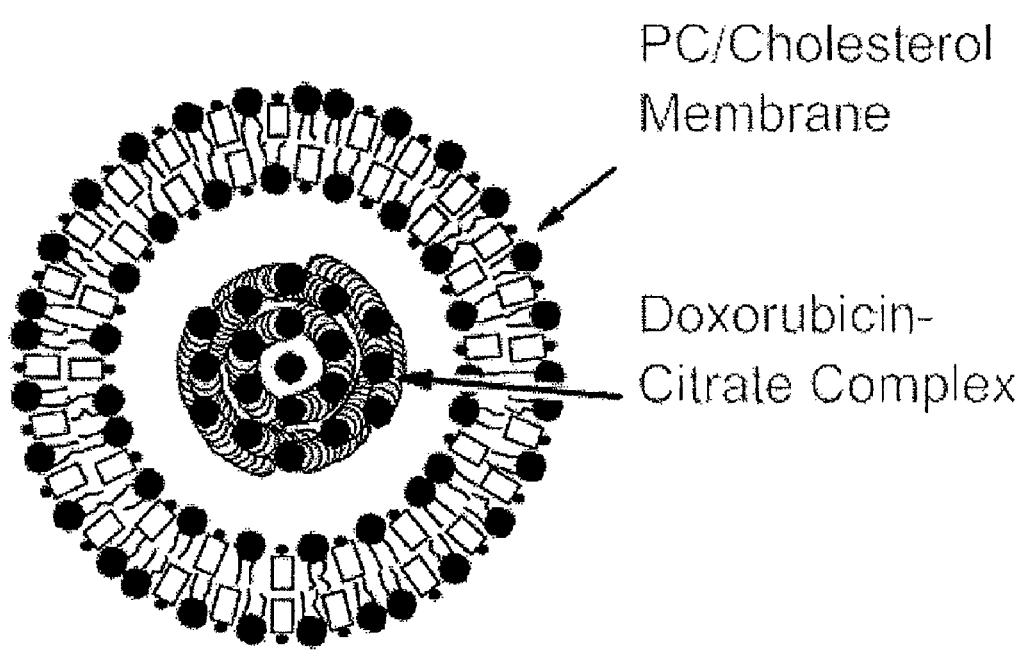
FIG. 1 is a representation of a nonpegylated liposome doxorubicin.

The present invention provides a method for treating metastatic breast cancer in an individual by administering to an individual in need thereof a dosing regimen which comprises administering to the individual nonpegylated liposomal doxorubicin, a taxane and a HER2/neu receptor antagonist, wherein the individual previously has been administered an anthracycline.

Suitable taxanes which may be used in the present invention include paclitaxel, docetaxel and albumin-bound paclitaxel. In one embodiment the taxane is paclitaxel. In one such embodiment paclitaxel is administered once weekly. In another embodiment the taxane is docetaxel or albumin-bound paclitaxel. In another embodiment the taxane is docetaxel. In one such embodiment docetaxel is administered every 3 weeks. In another embodiment the taxane is albumin-bound paclitaxel. In one such embodiment albumin-bound paclitaxel is administered every 3 weeks.

Suitable HER2/neu receptor antagonists which may be used in the present invention include trastuzumab, trastuzumab conjugates such as trastuzumab-DM1 and pertuzumab. In one embodiment, the HER2/neu receptor antagonist is trastuzumab. In one embodiment, the HER2/neu receptor antagonist is trastuzumab-DM1. In one embodiment, the HER2/neu receptor antagonist is pertuzumab.

As used herein, the term "concomitant" refers to events that occur with 48 hours of each other. Thus, when nonpegylated liposomal doxorubicin and trastuzumab are administered "concomitantly," they are administered with 48 hours of each other.

In one embodiment, where the HER2/neu receptor antagonist is trastuzumab, the present invention provides a method for treating metastatic breast cancer in an individual who has previously been administered an anthracycline by administering to the individual a dosing regimen comprising six consecutive 3-week long treatment cycles, wherein nonpegylated liposomal doxorubicin is administered on day 1 of each treatment cycle, a taxane is administered on day 1 of each treatment cycle, and trastuzumab is administered on day 1 of the first treatment cycle and every week thereafter. In one such embodiment, the nonpegylated liposomal doxorubicin and the trastuzumab are administered concomitantly.

In another embodiment, where the HER2/neu receptor antagonist is trastuzumab, the present invention provides a method for treating metastatic breast cancer in an individual who has previously been administered an anthracycline by administering to the individual a dosing regimen comprising six consecutive 3-week long treatment cycles, wherein nonpegylated liposomal doxorubicin is administered at a dose level of from 30 mg/m$^2$ to 75 mg/m$^2$ on day 1 of each treatment cycle, a taxane is administered at a dose level of from 50 mg/m$^2$ to 250 mg/m$^2$ on day 1 of each treatment cycle, and trastuzumab is administered at a dose level of from 3 mg/kg to 5 mg/kg as a loading dose on day 1 of the first treatment cycle and every week thereafter at a dose level of from 1 mg/kg to 3 mg/kg. In one such embodiment, the nonpegylated liposomal doxorubicin and the trastuzumab are administered concomitantly.

In another embodiment, where the HER2/neu receptor antagonist is trastuzumab, the present invention provides a method for treating metastatic breast cancer in an individual who has previously been administered an anthracycline by administering to the individual a dosing regimen comprising six consecutive 3-week long treatment cycles, wherein (a) nonpegylated liposomal doxorubicin is administered at a dose level of from 40 mg/m$^2$ to 75 mg/m$^2$ doxorubicin on day 1 of each treatment cycle; (b) a taxane is administered (i) at a dose level of from 60 mg/m$^2$ to 90 mg/m$^2$ on day 1 of each treatment cycle and every week thereafter, (ii) at a dose level of from 60 mg/m$^2$ to 90 mg/m$^2$ on day 1 of each treatment cycle, or (iii) at a dose level of from 150 mg/m$^2$ to 250 mg/m$^2$ on day 1 of each treatment cycle; and (c) trastuzumab is administered at a dose level of from 3 mg/kg to 5 mg/kg as a loading dose on day 1 of the first treatment cycle and every week thereafter at a dose level of from 1 mg/kg to 3 mg/kg. In one such embodiment, the nonpegylated liposomal doxorubicin and the trastuzumab are administered concomitantly.

In another embodiment, where the HER2/neu receptor antagonist is trastuzumab, the present invention provides a method for treating metastatic breast cancer in an individual who has previously been administered an anthracycline by administering to the individual a dosing regimen comprising six consecutive 3-week long treatment cycles, wherein (a) nonpegylated liposomal doxorubicin is administered at a dose level of about 50 mg/m$^2$ doxorubicin on day 1 of each treatment cycle; (b) a taxane is administered (i) at a dose level of about 80 mg/m$^2$ on day 1 of the first treatment cycle and every week thereafter; (ii) at a dose level of about 75 mg/m$^2$ on day 1 of each treatment cycle, or (iii) at a dose level of from 200 mg/m$^2$ to 250 mg/m$^2$ on day 1 of each treatment cycle; and (c) trastuzumab is administered at a dose level of about 4 mg/kg as a loading dose on day 1 of the first treatment cycle and every week thereafter at a dose level of about 2 mg/kg. In one such embodiment, wherein the taxane is paclitaxel, paclitaxel is administered at a dose level of about 80 mg/m$^2$ on day 1 of the first treatment cycle and every week thereafter. In another such embodiment, wherein the taxane is docetaxel, docetaxel is administered at a dose level of about 75 mg/m$^2$ on day 1 of each treatment cycle. In another embodiment, wherein the taxane is albumin bound paclitaxel, albumin-bound paclitaxel is administered at a dose level of 150 mg/m$^2$ to 250 mg/m$^2$ on day 1 of each treatment cycle. In another embodiment, wherein the taxane is albumin bound paclitaxel, albumin-bound paclitaxel is administered at a dose level of 200 mg/m$^2$ to 250 mg/m$^2$ on day 1 of each treatment cycle. In one such embodiment, the nonpegylated liposomal doxorubicin and the trastuzumab are administered concomitantly.

In another embodiment, the present invention provides a method for treating metastatic breast cancer in an individual comprising administering to an individual in need thereof a dosing regimen which comprises administering to the individual nonpegylated liposomal doxorubicin, trastuzumab and a chemotherapeutic agent selected from the group consisting of capecitabine, vinorelbine, gemcitabine and carboplatin, wherein said individual previously has been administered an anthracycline. In one such embodiment, the nonpegylated liposomal doxorubicin and the trastuzumab are administered concomitantly.

As discussed above, doxorubicin and trastuzumab are known to be cardiotoxic. In fact, the risk of cardiotoxicity from their combined use is such that non-liposomal doxorubicin may not be administered in combination with trastuzumab. Instead, the two chemotherapeutic agents may be administered concomitantly in combination only when the doxorubicin is in liposomal form. Even then, where the doxorubicin is in pegylated liposomal form, the risk of cardiotoxicity is greater than that from the use of either chemotherapeutic agent alone. Moreover, the already enhanced risk of cardiotoxicity from treatment with doxorubicin and trastuzumab is believed to be enhanced still further for patients who have received prior treatment with an anthracycline, due to accumulated doxorubicin dosing.

Administration of non-liposomal doxorubicin and trastuzumab to patients who have received prior treatment with an anthracycline is associated with an increased risk of developing cardiotoxicity during or after the dosing regimen.

In one embodiment of the present invention the dosing regimen does not substantially increase the likelihood that the individual will develop cardiotoxicity during or after the dosing regimen. In one such embodiment of the present invention the dosing regimen does not increase the likelihood that the individual will develop cardiotoxicity during or after the dosing regimen by more than 10%. In another such embodiment, the dosing regimen does not increase the likelihood that the individual will develop cardiotoxicity during or after the dosing regimen by more than 5%. In yet another such embodiment, the dosing regimen does not increase the likelihood that the individual will develop cardiotoxicity during or after the dosing regimen by more than 3%.

In one embodiment of the present invention the dosing regimen does not substantially increase the likelihood that the individual will develop a symptom of cardiotoxicity during or after the dosing regimen. In one such embodiment the symptom is reduced resting left ventricular ejection fraction.

In another embodiment of the present invention the dosing regimen does not substantially increase the likelihood that the individual will develop congestive heart failure during or after the dosing regimen. In one such embodiment of the present invention the dosing regimen does not increase the likelihood that the individual will develop congestive heart failure during or after the dosing regimen by more than 10%. In another such embodiment, the dosing regimen does not increase the likelihood that the individual will develop congestive heart failure during or after the dosing regimen by more than 5%. In yet another such embodiment, the dosing regimen does not increase the likelihood that the individual will develop congestive heart failure during or after the dosing regimen by more than 3%.

In one variation, the dosing regimen does not substantially increase the likelihood that the individual will develop New York Heart Association Class III or IV congestive heart failure during or after the dosing regimen. In one such embodiment of the present invention the dosing regimen does not increase the likelihood that the individual will develop New York Heart Association Class III or IV congestive heart failure during or after the dosing regimen by more than 10%. In another such embodiment, the dosing regimen does not increase the likelihood that the individual will develop New York Heart Association Class III or IV congestive heart failure during or after the dosing regimen by more than 5%. In yet another such embodiment, the dosing regimen does not increase the likelihood that the individual will develop New York Heart Association Class III or IV congestive heart failure during or after the dosing regimen by more than 3%.

In another embodiment of the present invention the dosing regimen does not substantially increase the likelihood that the individual will develop a symptom of congestive heart failure during or after the dosing regimen. In one such embodiment the symptom is dyspnea, tachycardia, cough, neck vein distention, cardiomegaly, hepatomegaly, paroxysmal nocturnal dyspnea, orthopnea or peripheral edema. In another such embodiment the symptom is dyspnea, tachycardia, neck vein distention, cardiomegaly, hepatomegaly, paroxysmal nocturnal dyspnea, orthopnea or peripheral edema.

In yet another embodiment of the present invention the dosing regimen does not substantially increase the likelihood that the individual will suffer cardiac death during or after the dosing regimen. In one such embodiment of the present invention the dosing regimen does not increase the likelihood that the individual will suffer cardiac death during or after the dosing regimen by more than 10%. In another such embodiment, the dosing regimen does not increase the likelihood that the individual will suffer cardiac death during or after the dosing regimen by more than 5%. In yet another such embodiment, the dosing regimen does not increase the likelihood that the individual will suffer cardiac death during or after the dosing regimen by more than 3%.

Elderly individuals have a higher rate of cardiac disease as well as chronic conditions, such as diabetes mellitus and hypertension, that may increase the risk of cardiac-related adverse events resulting from anthracycline administration. In one embodiment, the individual treated with a dosing regimen according to the present invention is at least 60 years of age. In one embodiment, the individual treated with a dosing regimen according to the present invention is at least 65 years of age. In one such embodiment, wherein the individual is at least 60 or at least 65 years of age, the individual has a condition that increases the risk of a cardiac-related adverse event resulting from anthracycline administration. In one embodiment the condition is diabetes or hypertension. In one such embodiment the condition is diabetes. In another such embodiment the condition is hypertension.

Palmar-plantar erythrodysesthesia, also known as hand-foot syndrome (HFS), is a side effect of certain chemotherapeutic agents that causes redness, swelling, and pain on the palms of the hands and/or the soles of the feet. HFS occurs when small amounts of chemotherapy leak out of the capillaries in the hands and feet. Once out of the blood vessels; the chemotherapy damages the surrounding tissues. Although less common, hand-foot syndrome can also occur on other areas of the skin, such as the knees and elbows.

The prescribing information provided with Doxil®, which is pegylated liposomal doxorubicin, reports that in the randomized ovarian cancer study, 50.6% of patients treated with Doxil® at 50 mg/m$^2$ every 4 weeks experienced HFS (developed palmar-plantar skin eruptions characterized by swelling, pain, erythema and, for some patients, desquamation of the skin on the hands and the feet), with 23.8% of the patients reporting HFS Grade 3 or 4 events, graded according to the NCI Common Toxicity Criteria Manual, Version 2.0 Jun. 1, 1999.

In another embodiment of the present invention the dosing regimen does not substantially increase the likelihood that the individual will develop palmar-plantar erythrodysesthesia during or after the dosing regimen. In one such embodiment, the dosing regimen does not increase the likelihood that the individual will develop palmar-plantar erythrodysesthesia during or after the dosing regimen by more than 10%. In another such embodiment, the dosing regimen does not increase the likelihood that the individual will develop palmar-plantar erythrodysesthesia during or after the dosing regimen by more than 8%. In yet another such embodiment, the dosing regimen does not increase the likelihood that the individual will develop palmar-plantar erythrodysesthesia during or after the dosing regimen by more than 6%. In a further embodiment, the dosing regimen does not increase the likelihood that the individual will develop Grade 3 or 4 events of palmar-plantar erythrodysesthesia during or after the dosing regimen by more than 5%. In one such embodiment, the dosing regimen does not increase the likelihood that the individual will develop Grade 3 or 4 events of palmar-plantar erythrodysesthesia during or after the dosing regimen by more than 4%. In yet another such embodiment, the dosing regimen does not increase the likelihood that the individual will develop Grade 3 or 4 events of palmar-plantar erythrodysesthesia during or after the dosing regimen by more than 3%. In yet another such embodiment, the dosing regimen does not increase the likelihood that the individual will develop Grade 3 or 4 events of palmar-plantar erythrodysesthesia during or after the dosing regimen by more than 2%.

In still another embodiment, the dosing regimen does not substantially increase the likelihood that the individual with develop either one of palmar-plantar erythrodysesthesia and congestive heart failure during or after the dosing regimen. In one such embodiment, wherein the dosing regimen comprises administering a chemotherapeutic agent selected from the group consisting of capecitabine, vinorelbine, gemcitabine and carboplatin, the dosing regimen does not increase the likelihood that the individual with develop either one of palmar-plantar erythrodysesthesia and congestive heart failure during or after the dosing regimen by more than 5% over that which would be expected based upon administration of the given chemotherapeutic agent alone.

As used herein, treatment that "does not substantially increase the likelihood" that the individual undergoing treatment will develop a particular condition, such as palmar-plantar erythrodysesthesia or congestive heart failure during such dosing regimen, refers to treatment that does not increase the probability that the individual undergoing treatment will develop the specified condition by more than 10%.

As used herein "previously administered" refers to administration of a drug, such as an anthracycline, at least 12 months before administration of the specified dosing regimen.

In one embodiment, the previous anthracycline administration is for the treatment of cancer. In one such embodiment, the previous anthracycline administration is for the treatment of breast cancer. The anthracycline previously administered to the individual may be any anthracycline that is approved for treatment in humans, such as, for example, doxorubicin, idarubicin, epirubicin, daunorubicin and valrubicin. Generally, the anthracycline previously administered to the individual is doxorubicin, idarubicin, epirubicin, or daunorubicin. In one embodiment, the anthracycline is doxorubicin. In one such embodiment, the doxorubicin previously administered to the individual is non-liposomal doxorubicin.

In one embodiment the previous anthracycline administration is adjuvant or neo-adjuvant administration of an anthracycline. In one such embodiment the previous anthracycline administration is adjuvant administration of an anthracycline. In another such embodiment the previous anthracycline administration is neo-adjuvant administration of an anthracycline.

In one embodiment the total amount of the anthracycline previously administered to said individual is less than or equal to 300 mg/m2 of doxorubicin or 600 mg/m2 of epirubicin. In one such embodiment the total amount of the anthracycline previously administered to said individual is from 50 mg/m2 to 450 mg/m2. In another such embodiment the total amount of the anthracycline previously administered to the individual is from 100 mg/m2 to 400 mg/m2. In still another such embodiment the total amount of the anthracycline previously administered to the individual is from 100 mg/m2 to 300 mg/m2. In yet another such embodiment the total amount of the anthracycline previously administered to the individual is from 200 mg/m2 to 300 mg/m2.

The total amount of anthracycline previously administered to the individual may vary depending upon the particular anthracycline previously administered. For example, where the previously administered anthracycline is epirubicin, the total amount of anthracycline previously administered may be up to, for example, 600 mg/m$^2$. On the other hand, where the previously administered anthracycline is doxorubicin, the total amount of anthracycline previously administered typically will not exceed 300 mg/m$^2$.

Typically, the previous administration of an anthracycline will have occurred at least 12 months prior to initiation of the dosing regimen of the present invention. In one such embodiment, the previous administration of an anthracycline will have occurred at least 18 months prior to initiation of the dosing regimen of the present invention. In another such embodiment, the previous administration of an anthracycline will have occurred at least 24 months prior to initiation of the dosing regimen of the present invention.

In another embodiment, the individual previously also has been administered trastuzumab. In one such embodiment the individual previously has been administered trastuzumab for a period of one to twelve months. In another such embodiment the individual previously has been administered trastuzumab for a period of nine to twelve months. In another such embodiment the individual previously has been administered trastuzumab for a period of six to nine months. In yet another such embodiment the individual previously has been administered trastuzumab for a period of three to six months. In still another such embodiment the individual previously has been administered trastuzumab for a period of one to three months. Typically, an individual is administered trastuzumab on a weekly basis throughout a treatment period. The typical dosing regimen for trastuzumab is an initial dose of 4 mg/Kg, followed by weekly administrations of 2 mg/Kg trastuzumab for a period of 12 months.

In one embodiment the metastatic breast cancer treated according to the present invention is HER2+ metastatic breast cancer.

A colony stimulating factor may be administered to individuals requiring supportive therapy for myelosuppression. Accordingly, in one embodiment the individual is administered, in addition to nonpegylated liposomal doxorubicin, a taxane and a HER2/neu receptor antagonist, a pharmaceutically effective amount of a colony stimulating factor. In one such embodiment the colony stimulating factor is a granulocyte colony stimulating factor, a macrophage colony stimulating factor or a granulocyte macrophage colony stimulating factor. In one such embodiment the colony stimulating factor is filgrastim, pegfilgrastim, sargramostim, lenograstim or molgramostim.

Chemotherapy-induced nausea and vomiting (CINV) is a common side-effect of chemotherapy treatment. An antiemetic agent may be administered to individuals requiring treatment for chemotherapy-induced nausea and/or vomiting. Accordingly, in one embodiment the individual is administered, in addition to nonpegylated liposomal doxorubicin, a taxane and a HER2/neu receptor antagonist, a pharmaceutically effective amount of an antiemetic agent. In one embodiment the antiemetic agent is a 5-HT3 receptor antagonist, a dopamine antagonist, an $NK_1$ receptor antagonist, a steroid or a cannabinoid. In one such embodiment the antiemetic agent is a 5-HT3 receptor antagonist. In one such embodiment the 5-HT3 receptor antagonist is dolasetron, granisetron, ondansetron, palonosetron or tropisetron. In another embodiment the antiemetic agent is a dopamine antagonist. In one such embodiment the dopamine antagonist is domperidone, droperidol, haloperidol, chlorpromazine, promethazine, prochlorperazine, metochlopramide or alizapride. In another embodiment the antiemetic agent is an $NK_1$ receptor antagonist. In one such embodiment the $NK_1$ receptor antagonist is aprepitant. In another embodiment the antiemetic agent is a cannabinoid. In one such embodiment the cannabinoid is cannabis, dronabinol, nabilone or sativex. In another embodiment the antiemetic agent is a steroid. In one such embodiment the steroid is dexamethasone.

Generally, nonpegylated liposomal doxorubicin is administered by infusion over 1 hour and is not given as a bolus injection. Doses of nonpegylated liposomal doxorubicin refer to the doxorubicin HCl content delivered in the nonpegylated liposomal doxorubicin injections.

The nonpegylated liposomal doxorubicin administered according to the present invention may be prepared according to the procedures described in U.S. Pat. No. 5,616,341, the entire disclosure of which is expressly incorporated by reference herein. One example of a nonpegylated liposomal doxorubicin is MYOCET®, a complex of doxorubicin-citrate encapsulated within the aqueous core of single lamellar liposomes that are composed of egg phosphatidylcholine:cholesterol (55:45 mole:mole). Encapsulation of doxorubicin can be achieved via an active loading process, which utilizes a proton concentration gradient, wherein the solution inside the liposome has an acidic pH and the solution outside the liposome has a basic pH. Once the doxorubicin is encapsulated, the internal complex is a flexible assembly of doxorubicin monomers stacked into fibers that are cross-linked by citrate into a hexagonal array with a 35 Å lattice repeat. The drug to lipid ratio of the encapsulated formulation is approximately 0.25:1 (wt:wt) and the pH is 6.5 to 8.5.

EXAMPLE 1

Preparation of Single Use Vial

Vial #1 Doxorubicin HCl for Injection is provided in glass vials sealed with butyl rubber stoppers and aluminum flip-off seals which contains:

| | |
|---|---|
| Doxorubicin HCl, USP | 50 mg |
| Lactose, NF (hydrous) | 250 mg |

Vial #2 Liposomes for Injection is provided in 2 ml type I flint glass tubing vial with grey stoppers siliconized with dimethicone and a flip-off seal which contains:

| | |
|---|---|
| Egg Phosphatidylcholine | 142.6 mg |
| Cholesterol, NF | 57.4 mg |
| Citrate Buffer (57.6 mg/mL) q.s. | 2 mL |

Vial #3 Buffer for Injection is provided in 5 ml type I molded glass vials with grey stoppers siliconized with dimethicone and a flip-off seal contains:

| | |
|---|---|
| Sodium Carbonate anhydrous, NF | 54.6 mg |
| Water for Injection, USP q.s. | 3.1 mL |

Each prepared vial of nonpegylated liposomal doxorubicin contains 50 mg of doxorubicin HCl, and each milliliter of nonpegylated liposomal doxorubicin contains:

| | |
|---|---|
| Doxorubicin HCl | 2.0 mg |
| Egg phosphatidylcholine | 5.4 mg |
| Cholesterol | 2.2 mg |
| Citric acid, monohydrate | 4.4 mg |
| Sodium carbonate | 2.2 mg |
| Lactose | 10.0 mg |
| Sodium Chloride Injection | 7.2 mg |

Cholesterol is controlled with an additional test for purity of not less than 95.0% by HPLC. Egg phosphatidylcholine is obtained by purifying egg yolk through extractions and chromatography. Doxorubicin HCl for Injection may contain around about 5 mg methylparaben, NF; in the nonpegylated liposomal doxorubicin, 0.2 mg methylparaben may be present. Generally the mean diameter of the liposomes is 100-230 nm.

During manufacture the product is sterilized using a 0.22 μm filter.

Generally, the citric acid buffer is prepared, the pH adjusted with sodium hydroxide solution, and filtered through a 0.2 μm nominal filter into a reactor. The liposomes are clarified by filtration and subsequently filtered through a 0.22 μm filter and stored under nitrogen pressure at 2-8° C. before filling. The vials are sterilized using dry heat and the stoppers are autoclaved. The particle size distribution is measured as one part of the in-process controls.

In preparation of the buffer, sodium carbonate is added to water for injection, the solution is mixed and filtered through a 0.22 μm filter into sterile tank and stored at room temperature prior to filling.

Step 1. Set Up
A. Turn on water bath and allow water to equilibrate at 58° C. (55 to 60° C.).
B. Remove Liposomal Doxorubicin Injection carton from the refrigerator.
Step 2. Reconstitute Doxorubicin HCl for Injection, USP (Vial No. 1)
A. Withdraw 20 mL sodium chloride injection (0.9%) and inject into each 50-mg vial of Doxorubicin HCl for Injection, USP intended for preparation (vial No. 1).
B. Shake well in the inverted position to ensure doxorubicin is fully dissolved.
Step 3. Heat in Water Bath
A. Heat the Doxorubicin HCl for Injection, USP (vial No. 1) in a water bath (55 to 60° C.) for 10 minutes (not to exceed 15 minutes).
While heating, proceed to Step 4.
Step 4. Adjust pH of Liposomes
A. Withdraw 1.9 mL of Liposomes for Injection (vial No. 2).
B. Inject into Buffer for Injection (vial No. 3). Pressure buildup may require venting.
C. Shake well.
Step 5. Add Liposomes to Doxorubicin
A. Using syringe, withdraw the entire vial contents of pH-adjusted liposomes (vial No. 3).
B. Remove Doxorubicin HCl for Injection, USP (vial No. 1) from the water bath.
SHAKE VIGOROUSLY. Then IMMEDIATELY (within 2 minutes) inject pH-adjusted liposomes into vial of heated 50 mg Doxorubicin HCl for Injection, USP (vial No. 1).
C. SHAKE VIGOROUSLY.
D. WAIT FOR A MINIMUM OF 10 MINUTES BEFORE USING.

EXAMPLE 2

The following study is being conducted to evaluate the safety and efficacy of the combination of non-pegylated liposomal doxorubicin (MYOCET®), paclitaxel and trastuzumab as first-line treatment in patients with HER2-overexpressing metastatic breast cancer. Inclusion criteria for the study are: (1) metastatic HER2+ breast cancer by FISH analysis; (2) no prior chemotherapy for metastatic disease; (3) measurable disease; and (4) normal left ventricular ejection fraction. Exclusion criteria are: (1) prior doxorubicin treatment exceeding 300 mg/m$^2$ or prior epirubicin treatment exceeding 600 mg/m$^2$; and (2) relapse within 12 months of completion of adjuvant trastuzumab, taxane or anthracycline therapy.

The primary objectives of this trial are to demonstrate the efficacy and cardiac safety of Myocet® when given in combination with trastuzumab and paclitaxel in patients with HER2+ metastatic breast cancer.

Within the population of patients who are administered a dosing regimen of Myocet®, trastuzumab and paclitaxel, there is a sub-population of patients that previously have been administered and anthracycline. With respect to the population of patients who are administered Myocet®; trastuzumab and paclitaxel, the dosing regimen does not substantially increase the risk of cardiotoxicity. Similarly, within the sub-population of patients that previously have been administered and anthracycline, administration of Myocet®, trastuzumab and paclitaxel does not substantially increase the risk of cardiotoxicity.

Primary Efficacy and Safety Endpoints:
Progression-Free Survival (PFS).
New York Heart Association Class III & IV congestive heart failure and cardiac death.

Secondary Efficacy and Safety Endpoints:
Overall Survival.
Objective Response Rate.
Safety Profile.

Progression Free Survival (PFS) is defined as the time from randomization until the date of disease progression or death due to any cause. For the primary analysis, PFS events will be the PFS events as defined by a blinded independent review board.

The cardiac safety endpoint is defined as New York Heart Association Class III or Class IV congestive heart failure and cardiac death. For the primary analysis, cardiac safety events will be the events as defined by a blinded independent review board.

Objective Response Rate is defined as the fraction of patients with complete or partial response as assessed by the Response Evaluation Criteria In Solid Tumors (RECIST). For the primary analysis, response will be the responses as defined by a blinded independent review board.

Overall Survival is defined as the time from randomization to the date of death.

The Safety Profile will compare treatment arms for worst grade adverse events; non-cardiac deaths and other serious adverse events; and worst grade laboratory abnormalities. Non-cardiac toxicity is assessed according to the National Cancer Institute (NCI) Common Terminology Criteria for Adverse Events (CTCAE) version 3.0.

Study Design, Randomization, Stratification

This is a Phase III, randomized, controlled, multi-center clinical trial in HER2+ patients with metastatic breast cancer. Myocet® is being administered (treatment arm A) at a dose of 50 mg/m$^2$ IV over one hour. For cycle 1, Trastuzumab is being given over 90 minutes 4 mg/kg IV on day 1, followed by 2 mg/kg over 30 minutes IV weekly on days 8 and 15. All subsequent cycles are 2 mg/kg days 1, 8 and 15. Treatment cycles are being repeated every 3 weeks unless precluded by disease progression or unacceptable toxicity. Paclitaxel is being administered at a dose of 80 mg/m$^2$ over one hour weekly IV. Dose escalation is not permitted, however, one dose reduction of Myocet® or paclitaxel may be made for specific hematological and non-hematological toxicity. Colony Stimulating Factor (CSF) therapy may be administered as needed.

Patients continue Myocet® treatment for a maximum of 6 cycles or until disease progression, the occurrence of unacceptable toxicity requiring discontinuation of study therapy, or for other reasons described in Criteria for Discontinuation, below.

Patients in both arms of the study continue treatment on trastuzumab and paclitaxel up to disease progression or until the occurrence of unacceptable toxicity requiring discontinuation of study therapy, or for other reasons described in Criteria for Discontinuation, below.

Criteria for Discontinuation
Study therapy is discontinued for any of the following:
1. Progressive disease.
2. Protocol-defined cardiotoxicity.
3. Any grade 3 non-hematological toxicity that does not reverse to grade 1 or less within 35 days of study drug administration (except for alopecia). If the toxicity can be attributable to a specific drug, then that drug should be held rather than removing the patient from the study.
4. Any grade 4 non-hematological toxicity (with exception of fever or infection), regardless of reversibility. If the toxicity can be attributable to a specific drug, then that drug should be held rather than removing the patient from the study.
5. Grade 4 neutropenia, thrombocytopenia or anemia that does not reverse to grade 2 or less within 35 days of study drug administration.
6. Patient non-compliance or significant protocol deviation.
7. Pregnancy.
8. An intercurrent illness that in the opinion of the investigator, would prevent completion of study-related evaluations.
9. At the discretion of the investigator(s) and/or sponsor, or at the request of the patient.

Randomization
Arm A
Myocet 50 mg/m$^2$ every 3 weeks
Paclitaxel 80 mg/m$^2$ weekly
Trastuzumab 2 mg/kg weekly (4 mg/kg loading, cycle 1 week 1 only)
OR
Arm B
Paclitaxel 80 mg/m$^2$ weekly
Trastuzumab 2 mg/kg weekly (4 mg/kg loading, cycle 1 week 1 only)

Stratification Factors
1. Hormone Receptor Status (Positive ER or PR versus others)
2. Age at randomization (>50 years versus $\leq$50 years)
3. Prior anthracycline use (yes versus no)
4. Geographical Area (North America versus Europe versus other)

Study Size
The target accrual is 332 randomized patients, 166 in each arm.

Study Population
Inclusion Criteria
Patients must meet all of the following criteria to be eligible for participation in the study:
1. Women 18 years of age or older.
2. Adenocarcinoma of the breast that is histologically or cytologically proven to show HER2 gene amplification positivity by fluorescence in situ hybridization (FISH).
3. Metastatic disease, using the American Joint Committee on Cancer staging criteria.
4. No prior chemotherapy for metastatic disease. Prior chemotherapy in adjuvant or neo-adjuvant setting is allowed if completed at least 1 year earlier. Prior adjuvant or neo-adjuvant chemotherapy within 12 months is allowed, if completed >4 weeks previously and if it did NOT include anthracyclines or taxanes or prior trastuzumab. Patients must not have received a cumulative dose of doxorubicin of greater than 300 mg/m$^2$ or epirubicin of greater than 600 mg/m$^2$.
5. Prior hormonal therapy is allowed in either the metastatic or adjuvant setting, but must be discontinued prior to first study drug administration.
6. At least one lesion that is measurable in one dimension (RECIST). Patients may have non-measurable disease as long as they have at least one measurable lesion.
7. Eastern Cooperative Oncology Group (ECOG) performance status 0-1 (Appendix B) and an anticipated life expectancy of $\geq$6 months.
8. Adequate bone marrow function:
   i. Absolute neutrophil count (ANC) >2,000/mm$^3$
   ii. Platelet count >100,000/mm$^3$ iii. Hemoglobin >10 g/Dl
9. Adequate liver and kidney function:
  i. Total bilirubin within normal limits for the institution
  ii. Aspartate aminotransferase (AST, SGOT) <3×ULN (or ≦5×ULN in presence of metastatic liver disease)
  iii. Alanine aminotransferase (ALT, SGPT) <3×ULN (or ≦5×ULN in presence of metastatic liver disease)
  iv. Serum creatinine <2.0 mg/dl
  v. Alkaline Phosphatase <3×ULN in the absence of bone metastases. If Alkaline Phosphatase >3×ULN in the presence of metastatic liver disease, or attributable to bone metastases, patients will be eligible.
10. Left ventricular ejection fraction (LVEF) within institutional normal range measured by MUGA or echocardiogram with MUGA being the preferred method. Note: with either method, the results will be centrally reviewed in a blinded fashion. Eligibility is based on site's initial reading.
11. Negative serum or urine β-hCG pregnancy test for women of childbearing potential within 7 days of study drug administration (i.e., women who are not surgically sterile or more than 2 years post-menopausal).
12. Adequate birth control measures by women of childbearing potential to prevent pregnancy during the study.
13. At least 4 weeks since major surgery, 3 weeks since radiotherapy, and discontinued hormone therapy (tamoxifen or aromatase inhibitors).
14. Written, signed and dated, informed consent. Note: Informed consent must be obtained at the time of patient screening, and before any procedures specifically related to this study are performed.

Exclusion Criteria

Patients meeting any of the following criteria are ineligible for participation in the study:
1. Prior chemotherapy or other systemic therapy other than hormonal therapy for metastatic disease.
2. Active, unresolved infection.
3. Prior adjuvant therapy with doxorubicin >300 mg/m$^2$ or epirubicin >600 mg/m$^2$.
4. Patients who develop metastatic disease ≦12 months after completing adjuvant trastuzumab (Herceptin), paclitaxel, docetaxel, or doxorubicin/epirubicin are considered to have had prior therapy for metastatic disease and are excluded from study participation.
5. Receiving concurrent hormonal therapy.
6. Prior radiation therapy ending less than three weeks before the start of study therapy.
7. Prior radiation therapy to the mediastinal area >3,500 cGy, or radiation to >25% of the bone marrow.
8. Symptomatic brain metastases, including patients requiring corticosteriod treatment or anti-convulsant medications for control of symptoms.
9. Active cardiac disease:
  i. Any prior myocardial infarction.
  ii. Current or history of documented congestive heart failure (CHF).
  iii. Current use of digitalis glycosides or ACE inhibitors for CHF, Note: ACE inhibitors can be used for hypertension.
  iv. Any prior history of arrhythmia or cardiac valvular disease requiring medications or considered clinically significant (e.g., under the care of a cardiologist).
  v. Current use of medications for treatment of arrhythmias or angina pectoris.
  vi. Current uncontrolled hypertension (diastolic >100 mmHg or systolic >200 mmHg).
  vii. Clinically significant pericardial effusion.
10. Prior malignancy within 5 years, except carcinoma in situ of the cervix or non-melanoma skin cancer.
11. Women who are pregnant or breast feeding.
12. Women of childbearing potential or sexual partner unwilling to employ adequate contraception.
13. History of hypersensitivity reaction to anthracyclines, trastuzumab, benzyl alcohol, G-CSF, Cremophor, eggs, or egg products.
14. Investigational agent(s) within 3 weeks of start of study therapy.
15. Known HIV infection.
16. Receiving any other standard or investigational treatment for cancer, or any other investigational agent for any indication.
17. Any concurrent medical or psychological condition that would limit the ability of the patient to provide informed consent or to comply with the obligations of the study.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for treating metastatic breast cancer in an individual previously treated with an anthracycline comprising administering to an individual in need thereof a dosing regimen which comprises at least one 3-week long treatment cycle, and wherein said individual is administered nonpegylated liposomal doxorubicin at a dose level of from 30 mg/m$^2$ to 75 mg/m$^2$ on day 1 of each treatment cycle, paclitaxel at a dose level of from 50 mg/m$^2$ to 250 mg/m$^2$ on day 1 of each treatment cycle, and trastuzumab at a dose level of from 3 mg/kg to 5 mg/kg as a loading dose on day 1 of the first treatment cycle and every week thereafter at a dose level of from 1 mg/kg to 3 mg/kg, and wherein said individual previously has been administered an anthracycline.

2. A method according to claim 1, wherein said previous administration of anthracycline was for the treatment of cancer.

3. A method according to claim 2, wherein said previous administration of anthracycline was for the treatment of breast cancer.

4. A method according to claim 1, wherein said anthracycline previously administered to said individual is selected from the group consisting of doxorubicin, idarubicin, epirubicin and daunorubicin.

5. A method according to claim 4, wherein said anthracycline previously administered to said individual is doxorubicin.

6. A method according to claim 4, wherein the total amount of said anthracycline previously administered to said individual is from 7 mg/m$^2$ to 450 mg/m$^2$.

7. A method according to claim 6, wherein the total amount of said anthracycline previously administered to said individual is from 100 mg/m$^2$ to 400 mg/m$^2$.

8. A method according to claim 1, wherein said dosing regimen does not substantially increase the likelihood that said individual will develop palmar-plantar erythrodysesthesia during said dosing regimen.

9. A method according to claim 1, wherein said dosing regimen does not substantially increase the likelihood that said individual will develop congestive heart failure during said dosing regimen.

10. A method according to claim 1, wherein said dosing regimen does not substantially increase the likelihood that said individual will suffer cardiac death during said dosing regimen.

11. A method according to claim 1, wherein said dosing regimen comprises six consecutive 3-week long treatment cycles.

12. A method according to claim 11, wherein said nonpegylated liposomal doxorubicin is administered at a dose level of about 50 mg/m$^2$ doxorubicin on day 1 of each treatment cycle, said paclitaxel[taxane] is administered at a dose level of about 80 mg/m$^2$ on day 1 of the first treatment cycle and every week thereafter or at a dose level of about 75 mg/m$^2$ on day 1 of each treatment cycle or at a dose level of from 200 mg/m$^2$ to 250 mg/m$^2$ on day 1 of each treatment cycle, and said trastuzumab is administered at a dose level of about 4 mg/kg on day 1 of the first treatment cycle and every week thereafter at a dose level of about 2 mg/kg.

13. A method according to claim 12, wherein said paclitaxel is administered at a dose level of about 80 mg/m$^2$ on day 1 of the first treatment cycle and every week thereafter.

* * * * *